United States Patent

Carr et al.

Patent Number: 5,227,167
Date of Patent: * Jul. 13, 1993

[54] LONG-TERM DELIVERY DEVICE INCLUDING HYDROPHOBIC LOADING DOSE

[75] Inventors: John P. Carr, Sunnyvale; James B. Eckenhoff, Los Altos; Terry L. Burkoth, Palo Alto, all of Calif.

[73] Assignee: ALZA Corporation, Palo Alto, Calif.

[*] Notice: The portion of the term of this patent subsequent to Sep. 3, 2008 has been disclaimed.

[21] Appl. No.: 842,939

[22] Filed: Feb. 27, 1992

Related U.S. Application Data

[63] Continuation-in-part of Ser. No. 714,544, Jun. 11, 1991, abandoned.

[51] Int. Cl.$^5$ .......................... A23K 1/18; A61K 9/22
[52] U.S. Cl. .................... 424/438; 424/422; 424/468; 604/892.1; 604/891.1; 604/890.1
[58] Field of Search ............................. 424/438, 473

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 3,995,632 | 12/1976 | Nakano et al. | 128/260 |
| 4,381,780 | 5/1983 | Holloway | 424/438 |
| 4,564,363 | 1/1986 | Bagnall et al. | 604/891 |
| 4,578,263 | 3/1986 | Whitehead | 424/438 |
| 4,595,583 | 6/1986 | Eckenhoff et al. | 424/15 |
| 4,612,186 | 9/1986 | Eckenhoff et al. | 424/15 |
| 4,643,731 | 2/1987 | Eckenhoff et al. | 604/892 |
| 4,704,118 | 11/1987 | Eckenhoff et al. | 604/892 |
| 4,729,793 | 3/1988 | Eckenhoff et al. | 106/169 |
| 4,772,474 | 9/1988 | Eckenhoff et al. | 424/465 |
| 4,844,984 | 7/1989 | Eckenhoff et al. | 424/438 |
| 4,927,419 | 5/1990 | Scully | 424/438 |
| 5,000,957 | 3/1991 | Eckenhoff et al. | 424/438 |
| 5,023,088 | 6/1991 | Wong et al. | 424/473 |
| 5,045,082 | 9/1991 | Ayer et al. | 604/892.1 |

FOREIGN PATENT DOCUMENTS

| | | | |
|---|---|---|---|
| 0321043 | 6/1989 | European Pat. Off. | |
| 86/00519 | 1/1986 | World Int. Prop. O. | 604/890.1 |

Primary Examiner—Thurman K. Page
Assistant Examiner—Raj Bawa
Attorney, Agent, or Firm—Jacqueline S. Larson; Paul L. Sabatine; Steven F. Stone

[57] ABSTRACT

The invention provides a dispensing device comprising a loading dose (first agent delivery means) for short-term and continuous delivery of an agent having a high potency, retained together with a long-term dispensing device (second agent delivery means) capable of a long-term and continuous delivery of agent. The combination of first and second agent delivery means provides a device in which a substantially constant dose of beneficial agent may be delivered to the environment of use over time. A rapid initial delivery of beneficial agent is followed by continuous and prolonged delivery of agent.

30 Claims, 3 Drawing Sheets

LONG-TERM DELIVERY DEVICE INCLUDING HYDROPHOBIC LOADING DOSE

This application is a continuation-in-part of U.S. application Ser. No. 07/714,544, filed on Jun. 11, 1991, now abandoned.

FIELD OF THE INVENTION

This invention pertains to the provision of a loading dose in long-term agent delivery devices. More particularly, the invention a relates to the provision of a beneficial agent loading dose as a part of a long-term beneficial agent delivery device. Such delivery devices find use in medical and veterinary delivery of medication and nutrients to humans and animals over a prolonged period of time.

BACKGROUND OF THE INVENTION

Agent delivery systems and devices which use an expansion means can deliver a beneficial agent to an environment of use over a period of hours, days, or months. The expansion means absorbs liquid, expands, and acts to drive out beneficial agent formulation from the interior of the device in a controlled manner.

Agent delivery devices which use an expansion means can be designed to deliver agent over a relatively short term, i.e., 20-25 days or less. Such devices generally comprise a highly permeable semipermeable membrane, together with a beneficial agent in a carrier s which is liquid, relatively non-viscous, and easily extruded by the action of the expansion means. The agent delivery profile of such a short-term device is shown, for example, in FIG. 12 of U.S. Pat. No. 4,595,583, the disclosure of which is hereby incorporated by reference. As shown in U.S. Pat. No. 4,643,731, the disclosure of which is hereby incorporated by reference, instantaneous concentration of beneficial agent obtained from short-term devices can be achieved by providing a loading dose, i.e., an initial, immediate, short-term dose of beneficial agent, prior to the onset of the continuous delivery provided by the osmotic pump device.

Agent delivery devices can alternatively be designed to deliver agent over a longer term, i.e., 25-30 days or greater, and especially 60-120 days or greater. Such devices generally comprise a slowly permeable semipermeable membrane, together with a beneficial agent in a carrier which is viscous or paste-like and extruded by the action of the expansion means over relatively longer times than shown by the short-term devices. The startup time of the device, that is, the time during which the device does not deliver beneficial agent, depends upon the rate at which the semipermeable membrane allows hydration of the system and the rate at which the expansion means becomes hydrated sufficiently to begin extrusion of the beneficial formulation. The agent delivery curve of a device designed to deliver a given dosage for 120 days is shown, for example, in FIG. 21 of U.S. Pat. No. 4,729,793.

The teachings of the prior art pertaining to loading doses of beneficial agent regarding short-term delivery devices do not provide a solution to the problem of the startup delay in long-term devices. Due to the kinetics of the release of loading doses for short-term devices, the loading doses are active for only a short time and do not sustain the concentration of beneficial agent during the startup period demonstrated by long-term devices. Those loading doses provided within the coating of a short-term device are not appropriate for use with long-term devices having a semipermeable membrane, as such coatings can interfere with the permeability of the semipermeable membrane, and thus interfere with the operation of the device.

Ruminant animals, including cattle, sheep, goats, deer, bison, camels and giraffes, and especially domestic animals such as cattle, sheep and goats, comprise an important group of animals that require periodic administration of medicines and nutrients. The medicines and nutrients are administered for the treatment and alleviation of various conditions and for improved health. Ruminants have a complex stomach generally having three or four compartments. The largest of the stomach compartments is the rumen, which acts as an important location for receiving and passing medicines and nutrients into other compartments, including the abomasum and the intestine.

One method of treating ruminants requires the repeated administration of medicines and nutrients at frequent time intervals. This form of treatment is inconvenient and expensive and does not lend itself to reliable therapy.

Prior art devices which have been designed to maintain continuous dosages of a beneficial agent for extended periods of time have the disadvantage of exhibiting a significant startup time between administration to the subject animal or human and the onset of agent delivery. Provision of effective dosages upon administration of the device has been obtained by prehydration (i.e., soaking) of the device prior to administration. For example, a prior art device which exhibits a three-week delay prior to onset of effective delivery of the desired agent can be soaked for three weeks at 40° C. or two months at room temperature prior to administration to the subject. Effective delivery of the desired agent thus begins upon administration.

Prehydration of a long-term device has several significant disadvantages. The soaking of a single device for a period of at least three weeks requires a processing step which is undesirable but which is likely to be manageable. The soaking of sufficient individual devices with which to supply an entire herd of animals can require a container the size of a swimming pool or a small lake. The active agent which is being delivered by the device is distributed into the water in which the device is soaked, and can require special treatment of the water before it can be released into ground or sewage waters. Additionally, if the device has limited stability (i.e., decomposition of the semipermeable membrane, density means, or other component of the device takes place over time), the time during which the device is prehydrated may limit the effective use in the subject animal. Or, prehydration of the device may require a special package, increasing the cost of the final, packaged device.

To overcome the limitations associated with the prior art delivery devices, a delivery device has been developed and is described and claimed in copending, commonly-assigned patent application U.S. Ser. No. 07/463,109, filed Jan. 10, 1990, now U.S. Pat. No. 5,045,082, to Ayer et al. for Long-Term Delivery Device Including Loading Dose. This delivery device comprises a semipermeable wall and a reservoir containing a beneficial agent formulation, an expansion means and, optionally, a density means. Additionally, it comprises another beneficial agent formulation in a loading dose that is at the surface of or within the device.

Although the device of U.S. Pat. No. 5,045,082 functions well when the beneficial agent is present in the loading dose in relatively large concentrations, when the agent is present in the loading dose in a relatively small concentration the device demonstrated an undesirably fast and unacceptably high release of the agent from the loading dose, thus providing an unacceptable release rate curve.

SUMMARY OF THE INVENTION

It has now been discovered by the inventors that the failure of the devices of U.S. Pat. No. 5,045,082 when small concentrations of beneficial agent are present was attributable to the hydrophilic nature of the fillers disclosed in U.S. Pat. No. 5,045,082 and used for the loading dose. When large amounts of agent are present, the agent itself acts to slow down the dissolution of the loading dose tablet and thus the release of the agent. However, when only small concentrations (of about 15 weight percent or less) of agent are present in the loading dose, the agent cannot act as a control on the rate of dissolution of the loading dose tablet, so that the hydrophilic filler material dissolves very quickly in the fluid environment of use and the agent is released at a rate far greater than that desired.

Accordingly, it is an object of this invention to provide a long-term dispensing device that quickly and continuously delivers a desired and effective amount of agent, followed by a continuous and sustained delivery of agent over a prolonged period of time.

Another object of the invention is to provide a long-term dispensing system comprising a first agent delivery means, comprising a relatively small concentration of a first beneficial agent, that quickly makes agent available and continues to make agent available during the period of time prior to the startup of a second agent delivery means, and a second agent delivery means that makes agent available for continuous and prolonged delivery, and thus provides a dispensing system that delivers agent quickly, continuously, and over a prolonged period of time when in operation in an environment of use.

Another object of the invention is to provide a first agent delivery means, comprising a relatively small concentration of a first beneficial agent, positioned within or at the surface of a long-term dispensing device comprising a second agent delivery means capable of long-term and continuous delivery of agent. The combination of first and second agent delivery means provides a device which exhibits beneficial agent rapidly delivered to the environment of use, together with continuous and prolonged delivery of agent, substantially eliminating the startup time associated with prior art devices.

Yet another object of the invention is to provide an improvement over the prior art by making available a dispensing device possessing controlled agent availability during a period of time during which the prior art dispensing devices did not make agent available to the environment of use.

Another object of the invention is to provide an improved beneficial agent dispensing device by providing a dispensing device which is easy to manufacture, inexpensive and easy to use, makes the desired agent quickly available, and provides constant and prolonged agent availability over time.

It is another object of the invention to provide a delivery device that can remain in the rumen of a ruminant for a prolonged period of time, providing not only rapid but continuous and prolonged delivery of a beneficial agent.

These and other objects, features and advantages of the invention will be more apparent to those skilled in the art from the following specification, taken in conjunction with the drawings and the accompanying claims.

The invention herein provides dispensing devices for the continuous delivery of a low concentration of a beneficial agent formulation to an environment of use over a prolonged period of time, together with methods of manufacture and use of such devices.

The present invention pertains to a dispensing device which comprises a loading dose (first agent delivery means) for rapid and continuous delivery of a first beneficial agent formulation to the environment of use, together with a long-term dispensing device (second agent delivery means) that provides continuous and prolonged delivery of a second beneficial agent formulation to the environment of use over time.

The loading dose provides a rapid and continuous delivery of a first beneficial agent formulation to the environment of use during the startup period of the long-term dispensing device. The loading dose comprises a hydrophobic compound for the slow dissolution of the loading dose to provide a continuous delivery of the first beneficial agent, which first beneficial agent is in relatively low concentrations in the loading dose, over the entire startup period of the long-term dispensing device. The loading dose is retained at the surface of or within the long-term dispensing device during the startup period of the long-term dispensing device and is exposed to the environment of use, releasing the beneficial agent formulation in a controlled manner. In one embodiment, the amount of beneficial agent provided by the loading dose is designed to mesh closely with the delivery rate of beneficial agent provided by the long-term dispensing device so that delivery of the beneficial agent is as uninterrupted and continuous as possible. In another embodiment, the loading dose is designed so that it provides a higher initial release of beneficial agent followed by a lower, constant release of beneficial agent that meshes closely with the delivery rate of beneficial agent provided by the long-term dispensing device.

The second agent delivery means provides continuous and prolonged delivery of a second beneficial agent formulation to the environment of use. The second agent delivery means comprises a semipermeable wall that surrounds and defines an internal lumen or compartment, an exit means in the dispensing device for delivery of the second beneficial agent formulation through the semipermeable wall from the compartment to the environment of use, and a second beneficial agent formulation in the lumen or compartment that provides a dispensable formulation to the environment of use. An expansion means (driving source) is provided in the lumen to displace the second beneficial agent formulation from the interior of the lumen through the exit means to the environment of use. In one preferred embodiment, a density means is included in the lumen and acts to retain the dispensing device in the environment of use. In an especially preferred embodiment, the exit means comprises a passageway through the density means which is adapted to contain the first agent delivery means.

DESCRIPTION OF THE DRAWINGS

The drawings are not drawn to scale, but are set forth to illustrate various embodiments of the invention. Like numbers refer to like structures. The drawing figures are as follows.

DETAILED DESCRIPTION OF THE INVENTION

Figure 1:
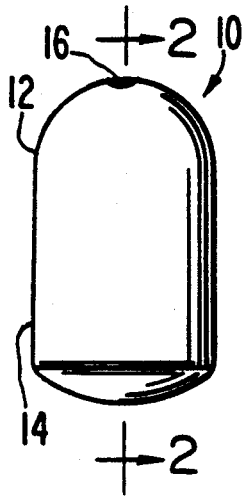
FIG. 1 is an external view of a delivery device designed and manufactured for administration of a beneficial agent to an animal.

The invention herein provides a device which is useful for delivering beneficial agent continuously to an environment of use over a prolonged period of time. The device of the invention is particularly suitable for the delivery of beneficial agents having a high potency such that the agent is present in the device, and particularly in the loading dose, in relatively low concentrations.

The preferred environment of use comprises the rumen of a ruminant animal. However, the devices are not restricted to use in ruminant animals or to a rumen environment of use. Long-term dispensing devices of the invention find use, for example, in humans or other animals. The environment of use can comprise a body cavity such as the peritoneum, vagina, or intestinal tract. The device may also be utilized as a subcutaneous implant. A single dispensing device or several dispensing devices can be administered to a subject during a therapeutic program.

The term "continuous" as used herein refers to delivery of a beneficial agent which varies little with the passage of time for the life of the device. Generally, the delivery of beneficial agent will vary by less than 50%, preferably by less than 20%, and more preferably by less than 10% over the period of agent delivery.

The "prolonged" delivery of agent refers to delivery of beneficial agent which continues for a period of 25 days or longer, generally 60 days or longer, and more generally for 120 days or longer.

The term "relatively low concentration" as used herein refers to a total concentration of beneficial agent in the first agent delivery means or loading dose of about 15 wt % (weight percent) or less, preferably of about 10 wt % or less. At this low concentration, the beneficial agent is not a controlling component in the dissolution or erosion of the first agent delivery means.

The term "agent" as used herein describes any beneficial agent or compound that can be delivered by a device herein to produce a beneficial and useful result. The term beneficial agent includes medicines or drugs, such as inorganic or organic drugs, anthelmintics, antiparasitic agents such as avermectin and ivermectin, antimicrobial agents, antibiotics, sulfa drugs, antiflea agents, rumen fermentation manipulators and ionophores, minerals and mineral salts such as selenium, antibloat agents, growth supplements, hormones, steroids, vaccines, proteins, estrus suppression agents such as melengestrol acetate, vitamins, antienteritis agents, nutritional supplements, and the like. It is to be understood that more than one beneficial agent may be incorporated into each of the beneficial agent formulations in a device of this invention, and that the use of the term "agent" in no way excludes the use of two or more such agents.

The first and second beneficial agent formulations may contain the same beneficial agent or they may contain different beneficial agents. However, it is a preferred embodiment that the first and second beneficial agent formulations contain the same beneficial agent. The first and second beneficial agents can comprise the same biological agent provided in different or dissimilar forms, but preferably the effective dose of the forms is adjusted to provide constancy of dosage over time.

The first beneficial agent formulation, or loading dose, provides a dosage of beneficial agent to the environment of use substantially throughout the time prior to the consistent release of the second beneficial agent formulation from the device. In the present invention, the first beneficial agent is chosen from those agents which have a high potency. By "high potency" is meant herein those beneficial agents that are delivered at a rate that is in the order of micrograms per kilogram of body weight of the host per day to achieve the desired therapeutic effect. In contrast, those agents which do not exhibit a high potency provide a desired therapeutic effect at a rate that is generally at least one order of magnitude higher. Because of their high potency, the agents must be present in the first agent delivery means in a relatively low concentration in order to provide the correct dosage. However, this low concentration creates a problem with prior loading dose formulations of hydrophilic carrier or filler material, because there is not sufficient amounts of a high potency beneficial agent in the formulation to assist in maintaining the integrity and slow dispersal of the loading dose over time. Without the presence of large amounts of the beneficial agent, the hydrophilic material will itself dissolve or erode or otherwise disperse rapidly in the fluid environment, causing the beneficial agent to be released over a period which is much shorter than the period required for the second agent delivery means to become hydrated and begin delivering second beneficial agent at the necessary rate. The result would be a delivery profile of a high potency agent that is not continuous but rather includes a period where very large concentrations of agent are delivered to the environment, followed by a period when substantially less or no amount of agent is being delivered. Additionally, the amount of beneficial agent released would be considerably greater than the desired dosage, which could result in overdosing or other adverse effects to the host animal.

Examples of a beneficial agent of high potency include, but are not limited to, antibiotics, such as quinolones, and hormones, such as somatotropins, estrogens, estrus suppression agents and progestogens such as melengestrol and melengestrol acetate. A presently preferred first beneficial agent of high potency is melengestrol acetate.

The first beneficial agent formulation comprises at least one first beneficial agent, having a high potency, homogeneously or heterogeneously dispersed or dissolved in an appropriate carrier means. The carrier means must include in at least a portion a hydrophobic material, and it may be entirely of a hydrophobic material or it may be a mixture of a hydrophobic material together with a hydrophilic material. In a presently preferred embodiment, the carrier means is a mixture of hydrophobic and hydrophilic materials.

The first beneficial agent formulation can be a solid, paste, gel, semisolid, or the like, or a thermosensitive material which provides a dispensable material in the environment of use. The first beneficial agent formulation can be provided in the form of a tablet or capsule, for example, and can be round, spheroid, toroid, cylindrical, square, and the like. The hydrophobic component of the carrier means which is added to the first beneficial agent to provide the first beneficial agent formulation is selected from hydrophobic materials such as natural waxes, synthetic waxes such as Fischer-Tropsch waxes, natural or synthetic resins, monoglycerides of fatty acids having a higher melting point such that they are in powdered or bead form for example, colloidal silicon dioxide, and the like. Such hydrophobic materials provide a slow dissolution of the first beneficial agent formulation in the environment of use to provide a continuous release of the first beneficial agent in the desired amount substantially throughout the time prior to the release of a second beneficial agent formulation. The hydrophilic component of the carrier means, when present in the means, is selected from hydrophilic materials which are well known in the art. Additional additives may optionally be included in the first beneficial agent formulation; these may include, for example, binders such as polyvinylpovidone, hydroxypropylmethylcellulose, guar gum, alginates such as sodium alginate, and the like; osmotic agents such as sodium chloride, sorbitol, and the like; and disintegration agents such as starch, polyplasdone XL, and the like.

The release rate of a specific loading dose tableted formulation in which the high potency beneficial agent is preferentially released by erosion can be approximated using the formula:

$$dm/dt = (A/2)(Co)$$

wherein
dm/dt = dosage rate of delivery, mg/day
K = erosion constant
A = surface area exposed to erosion process
Co = drug loading of beneficial agent in formulation It can be seen that varying the exposed surface area, A, and/or drug loading, Co, will vary the release rate for a given first beneficial agent formulation.

The second beneficial agent formulation provides a long-term constant dosage of a dispensable formulation including at least one second beneficial agent. The second beneficial agent formulation is urged from the lumen to the environment of use by the action of an expansion means. The second beneficial agent formulation may be in liquid, semi-solid or thermoresponsive form. In a preferred embodiment, the second beneficial agent is homogeneously or heterogeneously dispersed or dissolved in a thermoresponsive composition. Exemplary thermoresponsive compositions are detailed in U.S. Pat. No. 4,772,474, the disclosure of which is incorporated herein by reference.

In one preferred embodiment, the first beneficial agent formulation provides beneficial agent in a dosage pattern to deliver a substantially constant dose of beneficial agent during the existence of the device. That is, the first beneficial agent formulation is designed to deliver less beneficial agent to the environment of use as the second beneficial agent formulation begins to deliver beneficial agent to the environment of use. For example, if the target dosage of the long-term dispensing device is delivery of 8 mg/day of beneficial agent, the first beneficial agent formulation quickly and consistently delivers 8 mg/day of beneficial agent to the environment of use. As the second beneficial agent formulation begins delivery of beneficial agent at a rate of 1 mg/day, the rate of delivery of agent by the first beneficial agent formulation drops to 7 mg/day, for a total delivery of beneficial agent to the environment of use of 8 mg/day. Similarly, as the second beneficial agent formulation begins delivery of beneficial agent at a rate of 2 mg/day, the rate of delivery of agent by the first beneficial agent formulation drops to 6 mg/day, thus maintaining a total delivery to the environment of use of 8 mg/day. As the delivery rate of the second beneficial agent formulation approaches 8 mg/day, the first beneficial agent delivery means is depleted, and the delivery rate of the first beneficial agent formulation drops to 0 mg/day.

In another preferred embodiment, the first beneficial agent formulation provides beneficial agent in a dosage pattern to deliver a higher dose of beneficial agent for an initial period of time, followed by a substantially constant dose of beneficial agent during the remaining existence of the device. That is, the first beneficial agent formulation is designed to deliver a large amount of beneficial agent initially to the environment of use and then less beneficial agent as the second beneficial agent formulation begins to deliver beneficial agent to the environment of use. For example, if the target dosage of the long-term dispensing device is delivery of 12 mg/day of beneficial agent for the first three days followed by 8 mg/day of beneficial agent for the remaining life of the device, the first beneficial agent formulation quickly delivers 12 mg/day to the environment of use for the first three days, after which it begins to consistently deliver 8 mg/day of agent. Then, as the second beneficial agent formulation begins delivery of beneficial agent at a rate of 1 mg/day, the rate of delivery of agent by the first beneficial agent formulation drops to 7 mg/day, for a total delivery of beneficial agent to the environment of use of 8 mg/day. Similarly, as the second beneficial agent formulation begins delivery of beneficial agent at a rate of 2 mg/day, the rate of delivery of agent by the first beneficial agent formulation drops to 6 mg/day, thus maintaining a total delivery to the environment of use of 8 mg/day. As the delivery rate of the second beneficial agent formulation approaches 8 mg/day, the first beneficial agent delivery means is depleted, and the delivery rate of the first beneficial agent formulation drops to 0 mg/day.

Referring now to the FIGURES:

FIG. 1 is an external view of a beneficial agent delivery device 10 designed and manufactured for administration of a beneficial agent to an animal, such as a ruminant animal. The delivery device 10 comprises a body 12 formed by a semipermeable wall 14 that surrounds and defines an internal lumen (not shown). The beneficial agent delivery device also comprises a passageway (not shown) which terminates at the semipermeable wall 14 and is covered by a retaining means 16.

Figure 2:
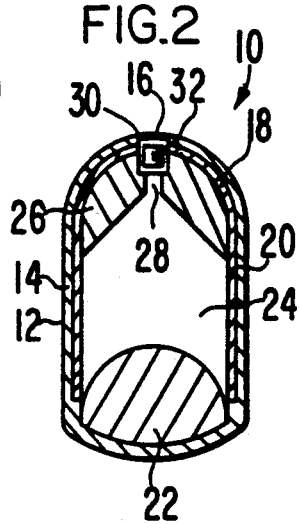
FIG. 2 is a cross-sectional view of the delivery device of FIG. 1 through A—A which illustrates the structure of the delivery device prior to or at the time of administration to an animal. Shown are a semipermeable outside wall, an internal capsule wall, a beneficial agent formulation, an expansion means, a density means, and a loading dose which is exposed to the environment of use.
Figure 3:
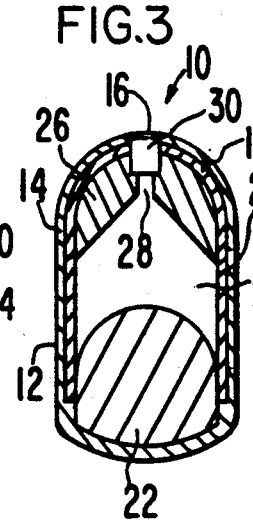
FIG. 3 is a view of the delivery device of FIG. 2 which illustrates the structure of the delivery device subsequent to administration of the device to an animal. The loading dose has been eroded by and dispersed into the environment of use, and expansion of the expansion means has commenced.
Figure 4:
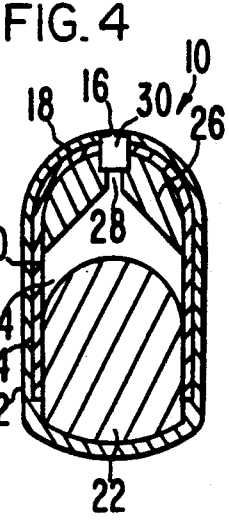
FIG. 4 is a view of the delivery device of FIG. 3 which illustrates the structure of the delivery device after continued use within the animal. The expansion of the expansion means has forced much of the beneficial agent formulation into the environment of use.

FIGS. 2-4 are cross-sectional views of the delivery device 10 of FIG. 1 through A—A, and illustrate the structure of the delivery device 10 prior to and subsequent to the time of administration to an animal. The device comprises a body 12, defined by an external semipermeable wall 14. The semipermeable wall 14 surrounds an optional internal capsule wall 18, and surrounds and defines an internal compartment or lumen 20. The semipermeable wall 14 is formed of a semipermeable composition; that is, a composition that is substantially permeable to the passage of fluid from the environment of use and is substantially impermeable to the passage of beneficial agent and other constituents found in the device. Materials which are appropriate for use in forming the semipermeable wall are known to the art and are set forth, for example, in U.S. Pat. No. 4,772,474, the disclosure of which has been incorporated by reference in its entirety.

The lumen 20 contains an expansion means 22 which acts to drive a second beneficial agent formulation 24 into the environment of use. Both the expansion means 22 and the second beneficial agent formulation 24 have a shape that corresponds to the internal shape of the lumen 20. The lumen 20 also contains a density means 26. The density means 26, also referred to as the densifier, is dense enough to retain the dispensing device in the environment of use. When the environment of use is the rumen of a ruminant, the density means is a necessary element of the dispensing device, and acts to retain the device in the rumen or reticular sac of the ruminant over a prolonged period of time. Appropriate density means are shown in, for example, U.S. Pat. Nos. 4,643,731 and 4,772,474, which have been incorporated by reference.

The expansion means 22 is positioned opposite the density means 26, with the second beneficial agent formulation 24 positioned between them. The expansion means 22, housed in the lumen 20, usually comprises a hydrogel composition which includes a swellable, expandable polymer and, optionally, an osmotically effective solute. The expansion means provides a driving source for delivering the second beneficial agent formulation 24 from the lumen 20 to the environment of use via the exit means 28. Materials which are appropriate for use in forming the expansion means are known to the art and are described in U.S. Pat. No. 4,772,474, for example, the disclosure of which has been incorporated by reference.

The density means 26 includes a passageway or exit means 28 which extends through the internal capsule wall 18 and the semipermeable wall 14 for metered delivery of the second beneficial agent formulation 24 to the environment of use. The exit means permits extrusion of second beneficial agent formulation from the lumen into the environment of use, and can be embodied by a passageway, aperture, bore, pore, and the like. Detailed descriptions of various passageways, the preferred maximum and minimum dimensions, and modes of manufacture are disclosed in U.S. Pat. Nos. 3,845,770 and 3,916,899, the disclosures of which are incorporated herein by reference in their entireties.

As shown in FIG. 2, the passageway also preferably includes a loading dose chamber 30, which, together with the retaining means 16, is designed to retain a loading dose 32, containing a formulation for the release of beneficial agent, in contact with the dispensing device 10 and in fluid contact with the environment of use. The retaining means 16, which covers the loading dose chamber, ensures that the first beneficial agent formulation is not separated from the long-term dispensing device or prematurely passed from the device. The retaining means 16 preferably intersects the exit means 28 at the surface of the device. The retaining means functions to keep the loading dose as an integral part of the dispensing device, but must also allow sufficient contact with the environment of use to permit consistent erosion or dispersion of the loading dose over time. The retaining means can comprise, for example, a perforated plate, a screen, a porous membrane such as an open-pore or blown-pore membrane, a perforated membrane, and the like. The material must be physically and chemically stable in the environment of use.

In a preferred embodiment, the retaining means preferably also functions to provide back-pressure to the second beneficial agent formulation extrusion means. In certain environments (e.g., the rumen), back pressure enhances the uniformity of the delivery profile.

Figure 5:
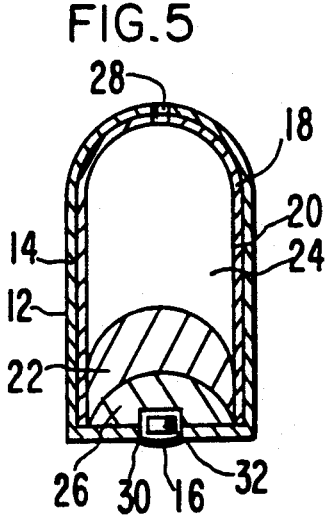
FIG. 5 is a view of a delivery device provided by the invention depicting an alternate internal structural configuration of elements comprising the delivery device.
Figure 6:
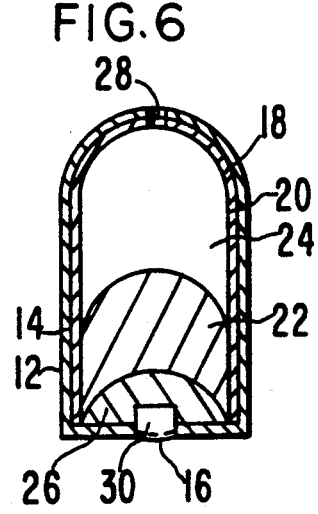
FIG. 6 is a view of the delivery device of FIG. 5 which illustrates the structure of the delivery device subsequent to administration of the device to an animal. The loading dose has been eroded by and dispersed into the environment of use, and expansion of the expansion means has commenced.
Figure 7:
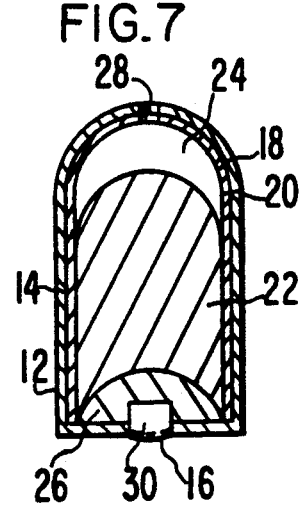
FIG. 7 is a view of the delivery device of FIG. 6 which illustrates the structure of the delivery device after continued use within the animal. The expansion of the expansion means has forced much of the beneficial agent formulation into the environment of use.

FIGS. 5-7 are cross-sectional views of another embodiment of a delivery device of the invention prior to and subsequent to administration to an animal. These drawings demonstrate an alternate internal structural configuration of elements comprising a delivery device. The density means 26 is located adjacent the expansion means 22, which in turn is located adjacent the second beneficial agent formulation 24. The passageway 28 comprises a bore or pore which extends through the optional internal capsule wall 18 and the semipermeable wall 14 for metered delivery of the second beneficial agent formulation 24 to the environment of use.

The loading dose compartment 30 is preferably integral to the exit means 28, but alternate configurations are possible. As shown in FIGS. 5-7, the loading dose compartment can be located at the surface of the device other than at the exit means. When the loading dose chamber is not integral to the exit means, it is preferably located adjacent the density means, if a density means is present. In a less preferred configuration, the loading dose chamber is located adjacent the expansion means or adjacent the second beneficial agent formulation. Such positioning is generally less preferred, as the presence of the loading dose chamber or physical properties of the loading dose formulation can inhibit the flux of fluids through the semipermeable wall into the lumen. The loading dose chamber 30 and retaining means 16 maintain the loading dose 32 in contact with the dispensing device and in contact with the environment of use.

Figure 8:
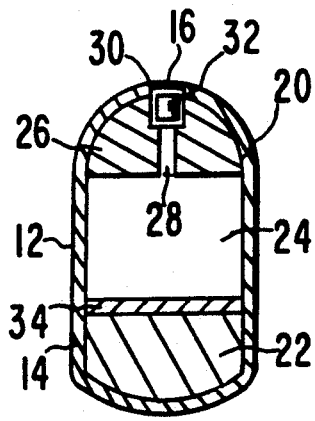
FIG. 8 is a view of a delivery device provided by the invention depicting an alternate internal structural configuration of elements comprising the delivery device. Shown are a semipermeable wall, a beneficial agent formulation, an expansion means, a means for optimizing delivery of the beneficial agent formulation, a density means, and a loading dose which is exposed to the environment of use.
Figure 9:
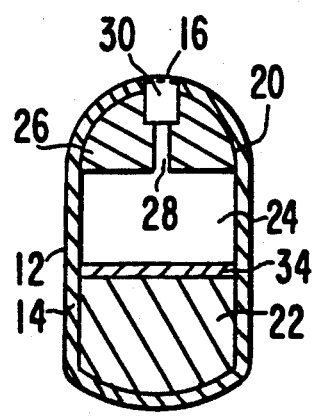
FIG. 9 is a view of the delivery device of FIG. 8 which illustrates the structure of the delivery device subsequent to administration of the device to an animal. The loading dose has been eroded by and dispersed into the environment of use, and expansion of the expansion means has commenced.
Figure 10:
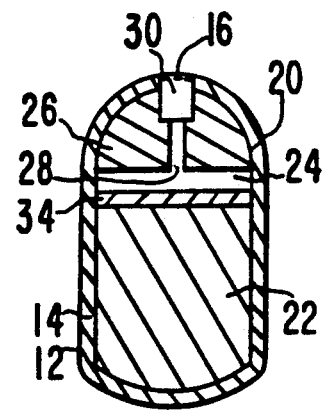
FIG. 10 is a view of the delivery device of FIG. 9 which illustrates the structure of the delivery device after continued use within the animal. The expansion of the expansion means has forced much of the beneficial agent formulation into the environment of use.

FIGS. 8-10 are cross-sectional views of a preferred embodiment of the delivery device of the invention prior to and subsequent to administration to an animal. The device comprises a body 12, defined by an external semipermeable wall 14. The semipermeable wall 14 surrounds an internal compartment or lumen 20. The lumen 20 contains an expansion means 22 and a second beneficial agent formulation 24, which are separated by a moveable barrier means 34. In a preferred embodiment of the delivery device herein, a moveable barrier means or lamina 34 is present within the lumen 20 and maintains the separate identities of the second beneficial agent formulation 24 and the expansion means 22. Such an embodiment is further described in U.S. Pat. Nos. 4,772,474 and 4,844,984, the disclosures of which are incorporated herein in their entireties. The moveable barrier means conveys the expanding force of the expansion means 22 against the second beneficial agent formulation, to assist in the expulsion of beneficial agent from the lumen into the environment of use. Each of the expansion means 22, second beneficial agent formulation 24, and the moveable barrier means 34 has a shape that corresponds to the internal shape of the lumen 20. The device also has a density means 26 with an exit means 28 which includes a loading dose chamber 30, a loading dose 32 and a retaining means 16.

The following examples are illustrative of the present invention. They are not to be construed as limitations of the scope of the invention. Variations and equivalents of these examples will be apparent to one skilled in the art in light of the present disclosure, the drawings, and the Claims herein. All percentages are weight/weight percent, and all temperatures are in degrees Celsius, unless otherwise noted.

EXAMPLE 1

A dispensing device with loading dose according to the present invention for the delivery of melengestrol acetate is manufactured as described below.

Semipermeable wall: 57 Weight percent (wt %) of cellulose acetate butyrate having a butyryl content of 17% and an acetyl content of 29% (Eastman) and 13 wt % cellulose acetate having an acetyl content of 39.8% (Eastman) were sized and combined with 20 wt % Citroflex-4 TM (tributyl citrate, Morflex, Inc.), 7.0 wt % Citroflex-2 TM (triethyl citrate, Pfizer, Inc.), and 3.0 wt % polyethylene glycol having a molecular weight of 400 (PEG 400, Union Carbide) in the bowl of a large mixer. After mixing for 20 minutes, the material was transferred to the feed hopper of an injection molder equipped with a suitable mold to produce a semipermeable cellulosic cup weighing 10.1 g and having the following dimensions: 7.9 cm height, 2.5 cm width, and wall thickness of 0.17 cm.

Expansion means: A blend of 62 wt % sodium carboxymethylcellulose, 30 wt % sodium chloride, 4.75 wt % hydroxypropylcellulose (Klucel EF®), 1 wt % hydroxypropylmethylcellulose E-5 (MW of 11,300), 1 wt % ferric oxide and 0.25 wt % magnesium stearate was made. 5.0 Grams of the blend were compressed under 10 tons of force on a Stokes bolus tablet press to form compressed hydrophilic tablets which conform to the internal diameter of the semipermeable cellulosic cups described above. A compressed hydrophilic expansion tablet was inserted into a semipermeable cellulosic cup.

Moveable barrier means: 50 Weight percent Multiwax TM 180M (Witco Chemical Co., Inc.), a food grade microcrystalline wax, was combined with 50 wt % Multiwax TM X145A microcrystalline wax (Witco Chemical Co., Inc.), and the mixture was heated to 85° C. in a Slauterback hot melt tank-pump. 1.9 Grams of the wax mixture were delivered to the cellulosic cup in laminated arrangement to the hydrophilic expansion member.

Second beneficial agent formulation: 99 Weight percent Multiwax TM X145A was melted using a hot plate, and the temperature was adjusted to 80° C. Melengestrol acetate (1 wt %) was added, using a high shear mixing apparatus. The temperature was maintained at 68° C. while 4.7 g (about 5.2 mL) aliquots of the melengestrol acetate formulation were delivered to individual cup assemblies. The melengestrol acetate formulation was allowed to cool and formed a lamina adjacent to the moveable barrier means in the cup.

First beneficial agent formulation (loading dose): 8 Weight percent melengestrol acetate, 59 wt % sodium alginate, 30 wt % microfine wax (Microfine Wax MF-2JH; Dura Commodities) and 2 wt % hydroxypropylmethylcellulose E-5 were thoroughly dry-blended together, after which anhydrous ethanol was added with further mixing. After the wet granulation mix was dried overnight and the dried granules were passed through a 30 mesh screen, they were mixed with 1 wt % magnesium stearate for five minutes. 100 Milligrams of the mix were compressed into a tablet.

Density Means: A sintered iron densifier, impregnated with wax to prevent corrosion and having a bore axially therethrough, was inserted into the open end of the cup assembly. The densifier was seated against the second beneficial agent formulation lamina. A melengestrol acetate loading dose tablet was inserted into the mouth of the bore of the densifier. The loading dose tablet was covered with an exit port screen having five orifices of 50 mil diameter each, and the screen was glued onto the densifier surface. The protruding lip of the cellulosic cup was heated until softened using a hot air gun, and the lip was crimped over the densifier to give a melengestrol acetate dispensing device of the present invention.

EXAMPLE 2

A prior art dispensing device without a loading dose for the delivery of melengestrol acetate is manufactured as described below.

The semipermeable wall, expansion means, moveable barrier, second beneficial agent formulation and density means were produced and a dispensing device was assembled as described in Example 1, except that a first beneficial agent loading dose and an exit port screen were not included.

EXAMPLE 3

The in vitro release rate of each of the melengestrol acetate dispensing devices of Examples 1 and 2 was determined as follows.

Figure 11:
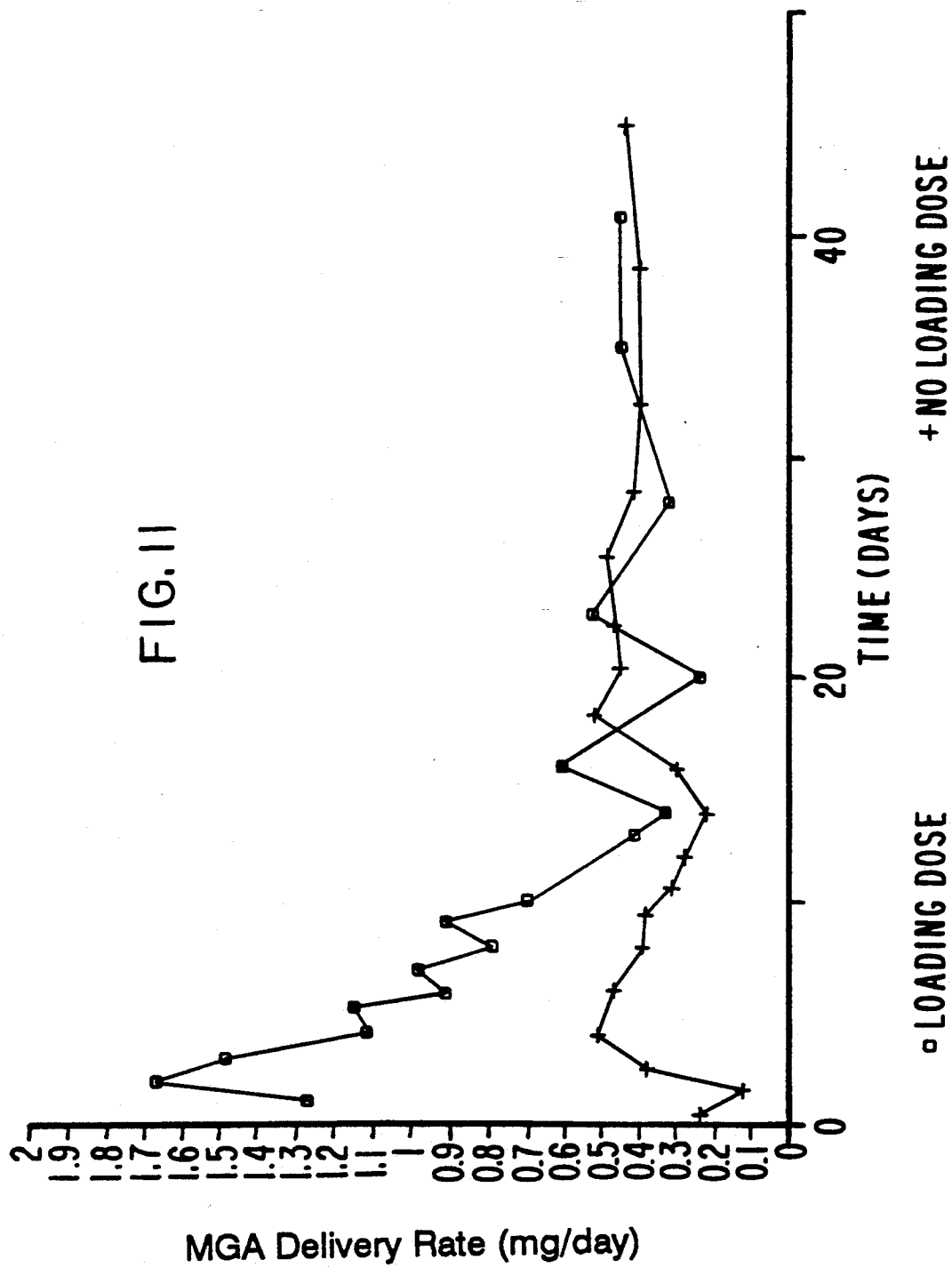
FIG. 11 depicts the delivery curves of (a) a melengestrol acetate long-term delivery device which does not include a loading dose, and which has not been prehydrated (shown by crosses); and (b) a melengestrol acetate long-term delivery device of this invention, which includes a loading dose (shown by squares). "MGA" stands for melengestrol acetate.

The dispensing device with loading dose from Example 1 was placed in an aqueous solution. The drug delivery of the loading dose of the device was determined, in vitro, by measuring, at intervals, the amount of drug formulation in the solution. After depletion of the loading dose, the device was replaced into an aqueous solution and the amount of drug formulation in the solution was measured periodically to determine the release rate. The in vitro release rate of the melengestrol acetate delivery device with a loading dose is shown, with squares, in FIG. 11.

The dispensing device without loading dose from Example 2 was placed in an aqueous solution. The drug delivery release rate was determined by removal of formulation from the solution at periodic intervals. The in vitro release rate of the melengestrol acetate delivery device without a loading dose is shown, with crosses, in FIG. 11.

EXAMPLE 4

A melengestrol acetate dispensing device with loading dose was prepared as in Example 1, and having the same composition except that the first beneficial agent formulation, or loading dose, comprised 4 wt % melengestrol acetate, 63 wt % sodium alginate (Kelcosol®), 30 wt % microfine wax MF-2JH, 2 wt % HPMC E-5 and 1 wt % magnesium stearate.

EXAMPLE 5

Another embodiment of a melengestrol acetate device according to the present invention was manufactured as described below.

Cellulosic cup with semipermeable wall: A semipermeable cellulosic cup was prepared having the same composition as and prepared according to the procedures of Example 1.

Expansion means: A blend of 55 wt % sodium carboxymethylcellulose, 26.5 wt % sodium chloride, 4.25 wt % hydroxypropylcellulose (Klucel EF®), 1 wt % hydroxypropylmethylcellulose E-5 (MW of 11,300), 13 wt % water and 0.25 wt % magnesium stearate was made. 5.0 Grams of the blend were compressed under 10 tons of force on a Stokes bolus tablet press to form compressed hydrophilic tablets which conform to the internal diameter of the semipermeable cellulosic cups described above. A compressed hydrophilic expansion tablet was inserted into a semipermeable cellulosic cup.

Moveable barrier means: 50 Weight percent Multiwax ™ 180M (Witco Chemical Co., Inc.), a food grade microcrystalline wax, was combined with 50 wt % Multiwax ™ X145A microcrystalline wax (Witco Chemical Co., Inc.), and the mixture was heated to 85° C. using a hot plate. 1.4 Grams of the wax mixture were delivered to the cellulosic cup in laminated arrangement to the hydrophilic expansion member.

Second beneficial agent formulation: 98.9 Weight percent Multiwax ™ X145A was melted using a hot plate, and the temperature was adjusted to 80° C. Melengestrol acetate (1.1 wt %) was added, using a high shear mixing apparatus. The temperature was maintained at 68° C. while 4.7 g (about 5.2 mL) aliquots of the melengestrol acetate formulation were delivered to individual cup assemblies. The melengestrol acetate formulation was allowed to cool and formed a lamina adjacent to the moveable barrier means in the cup.

First beneficial agent formulation (loading dose): 8 Weight percent melengestrol acetate, 59 wt % polyethylene oxide 7500K (Polyox® 303), 30 wt % microfine wax (Microfine Wax MF-2JH; Dura Commodities) and 2 wt % hydroxypropylmethylcellulose E-5 were thoroughly dry-blended together, after which anhydrous ethanol was added with further mixing. The wet granulation was passed through a 20 mesh screen. After the wet granulation mix was dried overnight and the dried granules were passed through a 20 mesh screen, they were mixed with 1 wt % magnesium stearate for five minutes. 100 Milligrams of the mix were compressed into a tablet.

Density Means: A sintered iron densifier, having a bore axially therethrough with a stepwise enlargement at the mouth, was impregnated with wax to prevent corrosion. A melengestrol acetate loading dose tablet was inserted into the step in the bore at the mouth of the desifier. The loading dose tablet was covered with a nylon exit port screen having five orifices of 50 mil diameter each, and the screen was snap-fitted onto the densifier. The densifier assembly was inserted into the open end of the cup assembly and seated against the second beneficial agent formulation lamina. The protruding lip of the cellulosic cup was heated until softened using a hot air gun, and the lip was crimped over the densifier to give a melengestrol acetate dispensing device of the present invention.

EXAMPLE 6

A prior art dispensing device without a loading dose for the delivery of melengestrol acetate is manufactured as described below.

The semipermeable wall, expansion means, moveable barrier, second beneficial agent formulation and density means were produced and a dispensing device was assembled as described in Example 5, except that a first beneficial agent loading dose and an exit port screen were not included.

EXAMPLE 7

Figure 12:
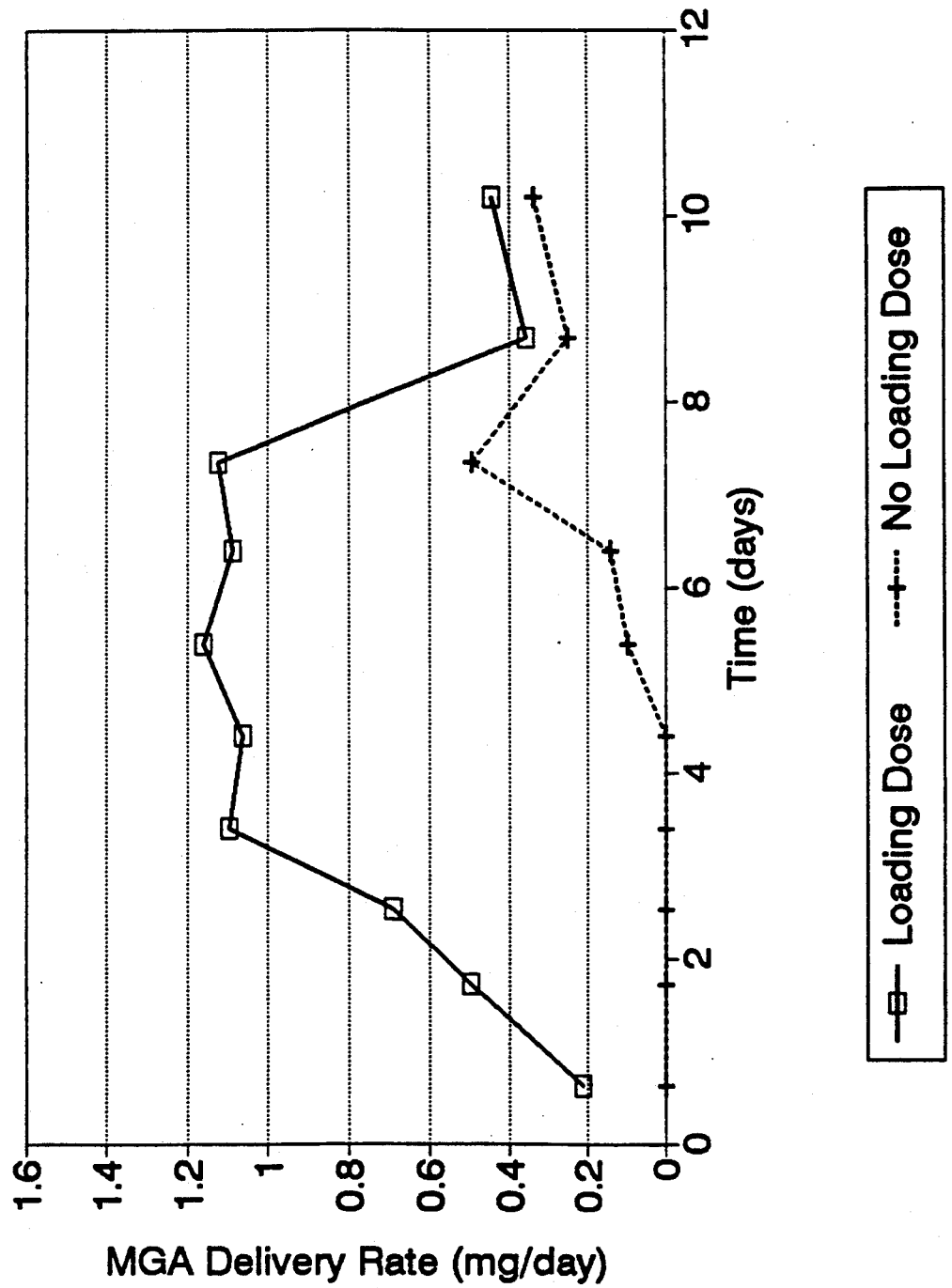
FIG. 12 depicts the delivery curves of (a) a melengestrol acetate long-term delivery device which does not include a loading dose, and which has not been prehydrated (shown by crosses); and (b) a melengestrol acetate long-term delivery device of this invention, which includes a loading dose (shown by squares).

The in vitro release rate of the melengestrol acetate dispensing devices of each of Examples 5 and 6 was determined following the procedures of Example 3. In FIG. 12, the in vitro release rate of the melengestrol acetate delivery device with a loading dose is shown, with squares (n=4), and the in vitro release rate of the melengestrol acetate delivery device without a loading dose is shown, with crosses.

Modifications of the above described process and apparatus will be apparent to those skilled in the art. Such modifications are intended to be within the spirit and scope of the following claims.

What is claimed is:

1. A single dispensing device for delivering a beneficial agent having a high potency to an environment of use for a prolonged period of time, the dispensing device comprising:
   (a) a first agent delivery means for making a first beneficial agent formulation quickly and continuously available to the environment of use, the first agent delivery means comprising:
      (1) a first beneficial agent formulation which comprises at least one beneficial agent having a high potency, in a concentration of about 15 wt % or less, and a carrier comprising in at least a portion a hydrophobic material, which first beneficial agent formulation releases the beneficial agent within the environment of use substantially throughout the time prior to the release of a second beneficial agent formulation; and
      (2) retaining means for retaining the first beneficial agent formulation at the surface of or within a second agent delivery means while exposing the first beneficial agent formulation and the second agent delivery means to the environment of use; and
   (b) a second agent delivery means for continuous and prolonged delivery of a second beneficial agent formulation to the environment of use, the second agent delivery means comprising:
      (1) a wall that surrounds and defines an internal lumen, the wall comprising a composition that is permeable to the passage of fluid and substantially impermeable to the passage of beneficial agent in a second beneficial agent formulation;
      (2) a second beneficial agent formulation in the lumen that provides a dispensable formulation including at least one beneficial agent to the environment of use;
      (3) an expansion means in the lumen for displacing the second beneficial agent formulation from the interior of the lumen to the environment of use after exposure to the environment of use; and
      (4) an exit means for delivery of the second beneficial agent formulation to the environment of use.

2. A dispensing device according to claim 1 wherein the release rates of beneficial agent from the first and second delivery means are selected to maintain the total agent delivery rate substantially constant over the prolonged time period.

3. A dispensing device according to claim 1 wherein the release rates of beneficial agent from the first and second delivery means are selected to provide a first delivery rate of agent for an initial portion of the prolonged time period followed by a second delivery rate of agent, the second delivery rate being lower than the first delivery rate and being maintained substantially constant over the remainder of the prolonged time period.

4. A dispensing device according to claim 1 which further comprises density means for maintaining the device within the rumen of a ruminant animal.

5. A dispensing device according to claim 4 wherein the exit means comprises a passageway through the density means.

6. A dispensing device according to claim 1 wherein the first beneficial agent formulation is disposed within the exit means.

7. A dispensing device according to claim 5 wherein the first beneficial agent formulation is disposed within the exit means.

8. A dispensing device according to claim 1 wherein the retaining means comprises a member selected from the group consisting of a perforated plate, a screen, a porous membrane, and a perforated membrane disposed between the environment of use and the first beneficial agent formulation.

9. A dispensing device according to claim 1 wherein the first beneficial agent formulation and the second beneficial agent formulation contain the same beneficial agent.

10. A dispensing device according to claim 9 wherein the beneficial agent is melengestrol acetate.

11. A dispensing device according to claim 1 wherein the first beneficial agent formulation and the second beneficial agent formulation contain different beneficial agents.

12. A dispensing device according to claim 1 wherein the first beneficial agent formulation is in a tablet form.

13. A single dispensing device for delivering melengestrol acetate to a ruminant animal for a prolonged period of time, the dispensing device comprising:

(a) a first agent delivery means for making a first melengestrol acetate formulation quickly and continuously available to the rumen of the ruminant animal, the first agent delivery means comprising:

(1) a first melengestrol acetate formulation which comprises melengestrol acetate, in a concentration of about 15 wt % or less, and a carrier comprising in at least a portion a hydrophobic material, which first melengestrol acetate formulation releases the melengestrol acetate within the rumen environment substantially throughout the time prior to the release of a second melengestrol acetate formulation; and (2) retaining means for retaining the first melengestrol acetate formulation at the surface of or within a second agent delivery means while exposing the first melengestrol acetate formulation and the second agent delivery means to the rumen environment; and (b) a second agent delivery means for continuous and prolonged delivery of a second melengestrol acetate formulation to the rumen environment, the second agent delivery means comprising:

(1) a wall that surrounds and defines an internal lumen, the wall comprising a composition that is permeable to the passage of fluid and substantially impermeable to the passage of melengestrol acetate in a second melengestrol acetate formulation;

(2) a second melengestrol acetate formulation in the lumen that provides a dispensable formulation of melengestrol acetate to the rumen environment;

(3) an expansion means in the lumen for displacing the second melengestrol acetate formulation from the interior of the lumen to the rumen environment after exposure to the rumen environment;

(4) density means for maintaining the device within the rumen; and (5) exit means for delivery of the second melengestrol acetate formulation to the rumen environment, where the exit means comprises a passageway through the density means and where the first melengestrol acetate formulation is disposed within the exit means.

14. A dispensing device according to claim 13 wherein the first melengestrol acetate formulation is in a tablet form.

15. A dispensing device according to claim 13 wherein the retaining means comprises a member selected from the group consisting of a perforated plate, a screen, a porous membrane, and a perforated membrane disposed between the rumen environment and the first melengestrol acetate formulation.

16. A dispensing device according to claim 14 wherein the retaining means comprises a member selected from the group consisting of a perforated plate, a screen, a porous membrane, and a perforated membrane disposed between the rumen environment and the first melengestrol acetate formulation.

17. A dispensing device according to claim 13 wherein the carrier further comprises a hydrophilic material.

18. A dispensing device according to claim 13 wherein the release rates of melengestrol acetate from the first and second delivery means are selected to provide a first delivery rate of melengestrol acetate for an initial portion of the prolonged time period followed by a second delivery rate of melengestrol acetate, the second delivery rate being lower than the first delivery rate and being maintained substantially constant over the remainder of the prolonged time period.

19. A method for administering a beneficial agent having a high potency to an environment of use for a prolonged period of time, which method comprises:

(a) introducing into the environment of use a single dispensing device, which device comprises:

(1) a first agent delivery means for making a first beneficial agent formulation quickly and continuously available to the environment of use, the first agent delivery means comprising:

(i) a first beneficial agent formulation which comprises at least one beneficial agent having a high potency, in a concentration of about 15 wt % or less, and a carrier comprising in at least a portion a hydrophobic material, which first beneficial agent formulation releases the beneficial agent within the environment of use substantially throughout the time prior to the release of a second beneficial agent formulation; and (ii) retaining means for retaining the first beneficial agent formulation at the surface of or within a second agent delivery means while exposing the first beneficial agent formulation and the second agent delivery means to the environment of use; and (2) a second agent delivery means for continuous and prolonged delivery of a second beneficial agent formulation to the environment of use, the second agent delivery means comprising:

(i) a wall that surrounds and defines an internal lumen, the wall comprising a composition that is permeable to the passage of fluid and substantially impermeable to the passage of beneficial agent in a second beneficial agent formulation;

(ii) a second beneficial agent formulation in the lumen that provides a dispensable formulation including at least one beneficial agent to the environment of use;

(iii) an expansion means in the lumen for displacing the second beneficial agent formulation from the interior of the lumen to the environment of use after exposure to the environment of use; and (iv) an exit means in the dispensing device for delivery of the second beneficial agent formulation to the environment of use;

(b) releasing beneficial agent from the first agent delivery means for an initial portion of the prolonged period of time; and (c) releasing beneficial agent from the second agent delivery means for a terminal portion of the prolonged period of time.

20. A method according to claim 19 wherein the release rates of agent from the first and second delivery means are selected to maintain the total agent delivery rate substantially constant over the prolonged period of time.

21. A method according to claim 19 wherein the dispensing device further comprises density means for maintaining the device within the rumen of a ruminant animal.

22. A method according to claim 21 wherein the exit means comprises a passageway through the density means.

23. A method according to claim 19 wherein the first beneficial agent formulation is disposed within the exit means.

24. A method according to claim 19 wherein the retaining means comprises a member selected from the group consisting of a perforated plate, a screen, a porous membrane, and a perforated membrane disposed between the environment of use and the first beneficial agent formulation.

25. A method according to claim 19 wherein the first beneficial agent formulation and the second beneficial agent formulation contain the same beneficial agent.

26. A method for administering melengestrol acetate to the rumen of a ruminant animal for a prolonged period of time, which method comprises:

(a) introducing into the rumen of the animal a single dispensing device, which device comprises:

(1) a first agent delivery means for making a first melengestrol acetate formulation quickly and continuously available to the rumen environment, the first agent delivery means comprising:

(i) a first melengestrol acetate formulation which comprises melengestrol acetate in a concentration of about 15 wt % or less, and a carrier comprising in at least a portion a hydrophobic material, which first melengestrol acetate formulation releases the melengestrol acetate within the rumen environment substantially throughout the time prior to the release of a second melengestrol acetate formulation; and (ii) retaining means for retaining the first melengestrol acetate formulation at the surface of or within a second agent delivery means while exposing the first melengestrol acetate formulation and the second agent delivery means to the rumen environment;

(2) a second agent delivery means for continuous and prolonged delivery of a second melengestrol acetate formulation to the rumen environment, the second agent delivery means comprising:
  (i) a wall that surrounds and defines an internal lumen, the wall comprising a composition that is permeable to the passage of fluid and substantially impermeable to the passage of melengestrol acetate in a second melengestrol acetate formulation;
  (ii) a second melengestrol acetate formulation in the lumen that provides a dispensable formulation including melengestrol to the rumen environment;
  (iii) an expansion means in the lumen for displacing the second melengestrol acetate formulation from the interior of the lumen to the rumen environment after exposure to the rumen environment;
  (iv) density means for maintaining the device within the rumen environment; and
  (v) exit means in the dispensing device for delivery of the second melengestrol acetate formulation to the rumen environment, where the exit means comprises a passageway through the density means and where the first melengestrol acetate formulation is disposed within the exit means;

(b) releasing melengestrol acetate from the first agent delivery means for an initial portion of the prolonged period of time; and (c) releasing melengestrol acetate from the second agent delivery means for a terminal portion of the prolonged period of time.

27. A method according to claim 26 wherein the first melengestrol acetate formulation is in a tablet form.

28. A method according to claim 26 wherein the retaining means comprises a member selected from the group consisting of a perforated plate, a screen, a porous membrane, and a perforated membrane disposed between the rumen environment and the first melengestrol acetate formulation.

29. A method according to claim 27 wherein the retaining means comprises a member selected from the group consisting of a perforated plate, a screen, a porous membrane, and a perforated membrane disposed between the rumen environment and the first melengestrol acetate formulation.

30. A method according to claim 26 wherein the release rates of melengestrol acetate from the first and second delivery means are selected to provide a first delivery rate of melengestrol acetate for an initial portion of the prolonged time period followed by a second delivery rate of melengestrol acetate, the second delivery rate being lower than the first delivery rate and being maintained substantially constant over the remainder of the prolonged time period.

* * * * *